United States Patent [19]

Dirlam

[11] 4,039,540
[45] Aug. 2, 1977

[54] 3-SUBSTITUTED QUINOXALINE-2-CARBOXAMIDE-1,4-DIOXIDES

[75] Inventor: John P. Dirlam, Gales Ferry, Conn.

[73] Assignee: Pfizer Inc., New York, N.Y.

[21] Appl. No.: 632,219

[22] Filed: Nov. 17, 1975

Related U.S. Application Data

[63] Continuation-in-part of Ser. No. 467,718, May 7, 1974, abandoned.

[51] Int. Cl.$^2$ .............. C07D 241/52; C07D 403/12; C07D 401/12
[52] U.S. Cl. .............. 260/250 QN; 260/268 BC; 424/250; 424/246; 424/248.51; 544/62; 544/80; 544/116; 544/119
[58] Field of Search ............ 260/250 Q, 247.1 L, 260/250 QN, 243 B, 268 BC

[56] References Cited

U.S. PATENT DOCUMENTS

| | | | |
|---|---|---|---|
| 3,558,624 | 1/1971 | Ley et al. | 260/250 QN |
| 3,598,820 | 8/1971 | Ley et al. | 260/250 QN |
| 3,644,360 | 2/1972 | Abu el Haj | 260/250 QN |
| 3,660,391 | 5/1972 | Ley et al. | 260/250 Q |
| 3,931,174 | 1/1976 | McFarland | 260/250 QN |

Primary Examiner—Donald G. Daus
Assistant Examiner—Mark L. Berch
Attorney, Agent, or Firm—Connolly and Hutz

[57] ABSTRACT

Compounds of the formula

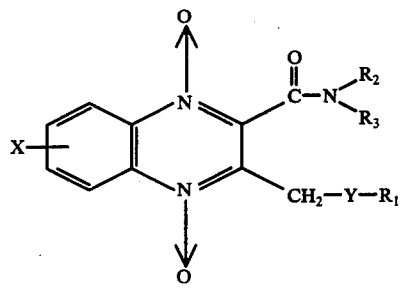

wherein X is a 6- or 7-position substituent selected from the group consisting of hydrogen, halogen, lower alkoxy, trifluoromethyl, methyl, lower alkyl sulfide, lower alkyl sulfoxide and lower alkyl sulfone; Y is S, SO or SO$_2$; R$_1$ is carbamyl(lower alkyl), carbo(lower alkoxy)-lower alkyl or monosubstituted alkyl having from 2 to 4 carbon atoms in the alkyl group wherein the substituent is selected from the group consisting of hydroxy, lower alkoxy, amino, mono(lower alkyl)amino, di(lower alkyl)amino, mono(lower alkyl)carbamyl, di(lower alkyl)carbamyl, halogen, mercapto, sulfo, lower alkyl sulfide, lower alkyl sulfoxide, lower alkyl sulfone, acetoxy, pyrrolidino, piperidino, morpholino, thiomorpholino, piperazino, N-(lower alkyl)piperazino, N-hydroxy(lower alkyl)piperazino, N-(lower alkanoyl)-piperazino and N-carbo(lower alkoxy)piperazino; R$_2$, when taken separately, is hydrogen or lower akyl; R$_3$, when taken separately, is hydrogen, lower alkyl or monosubstituted lower alkyl wherein the substituent is phenyl, amino, mono(lower alkyl)amino, di(lower alkyl)amino, pyrrolidino, piperidino, morpholino, N-(lower alkyl)piperazino, N-hydroxy(lower alkyl)-piperazino, N-(lower alkanoyl)piperazino, N-carbo(-lower alkoxy)piperazino, pyrrolo, piperazino, imidazolidino, hydroxy, lower alkoxy, carboxy, carbo(-lower alkoxy), carbamyl, mono(lower alkyl)carbamyl, thio(lower alkyl), di(lower alkyl)carbamyl, lower alkanoyloxy or lower alkanoylamino and R$_2$ and R$_3$, when taken together with the nitrogen atom to which they are attached, form a member selected from the group consisting of pyrrolo, pyrrolidino, piperidino, morpholino, thiomorpholino, piperazino, N-(lower alkyl)piperazino, N-hydroxy(lower alkyl)piperazino, N-(lower alkanoyl)-piperazino and N-carbo(lower alkoxy)piperazino and the pharmaceutically acceptable acid addition salts of those compounds wherein at least one of R$_1$ and R$_3$ is substituted lower alkyl wherein the substituent is a basic group; methods for their preparation; and their use as antibacterial agents and as agents for promoting growth and improving feed efficiency of animals.

10 Claims, No Drawings

3-SUBSTITUTED QUINOXALINE-2-CARBOXAMIDE-1,4-DIOXIDES

CROSS-REFERENCE TO RELATED APPLICATION

This application is a continuation-in-part of application Ser. No. 467,718, filed May 7, 1974, now abandoned.

BACKGROUND OF THE INVENTION

This invention relates to 3-substituted quinoxaline-2-carboxamide-1,4-dioxides which are useful antibacterial agents for the control of various pathogenic microorganisms and as animal growth promotants.

Various analogs of the compounds of the present invention are known in the prior art to be useful for such purposes. Typical examples of these prior art analogs are disclosed in U.S. Pat. Nos. 3,644,360 and 3,558,624. The former patent describes compounds having the above formula wherein $R_1$ is lower alkyl; and the latter patent, compounds in which —Y—$R_1$ is, inter alia, -S-alkanoyl or -S-benzoyl. Whereas these prior art analogs do have useful activity for the stated purposes, it has been found that they display certain toxic side effects when used, for example, in animal feeds. Unexpectedly, it has been found that the compounds of the present invention display a marked unexpected reduction in these side effects and may, therefore, be used with a higher degree of safety or in larger amounts for more rapid control of various pathogenic microorganisms and/or as animal growth promotants.

SUMMARY OF THE INVENTION

It has been found that a series of 3-substituted quinoxaline-2-carboxamide-1,4-dioxides are valuable antibacterial agents. These compounds have the formula

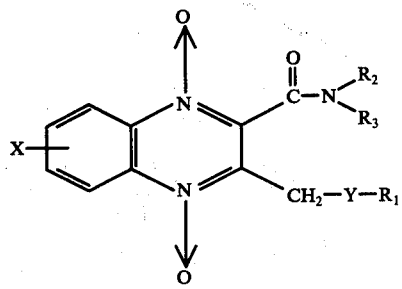

wherein X is a 6- or 7-position substituent selected from the group consisting of hydrogen, halogen, lower alkoxy, trifluoromethyl, methyl, lower alkyl sulfide, lower alkyl sulfoxide and lower alkyl sulfone; Y is S, SO or $SO_2$; $R_1$ is selected from the group consisting of carbamyl(lower alkyl), carbo(lower alkoxy)lower alkyl and monosubstituted alkyl having from 2 to 4 carbon atoms in the alkyl group wherein the substituent is selected from the group consisting of hydroxy, lower alkoxy, amino, mono(lower alkyl)amino, di(lower alkyl)amino, mono(lower alkyl)carbamyl, di(lower alkyl)carbamyl, halogen, mercapto, sulfo, lower alkyl sulfide, lower alkyl sulfoxide, lower alkyl sulfone, acetoxy, pyrrolidino, piperidino, morpholino, thiomorpholino, piperazino, N-(lower alkyl)piperazino, N-hydroxy(lower alkyl)piperazino, N-(lower alkanoyl)piperazino and N-carbo(lower alkoxy)piperazino; $R_2$, when taken separately, is hydrogen or lower alkyl; $R_3$, when taken separately, is hydrogen, lower alkyl or monosubstituted lower alkyl wherein the substituent is phenyl, amino, mono(lower alkyl)amino, di(lower alkyl)amino, pyrrolidino, piperidino, morpholino, N-(lower alkyl)piperazino, N-hydroxy(lower alkyl)piperazino, N-(lower alkanoyl)piperazino, N-carbo(lower alkoxy)piperazino, pyrrolo, piperazino, imidazolidino, hydroxy, lower alkoxy, thio(lower alkyl), carboxy, carbo(lower alkoxy), carbamyl, mono(lower alkyl)carbamyl, di(lower alkyl)carbamyl, lower alkanoyloxy or lower alkanoylamino and $R_2$ and $R_3$, when taken together with the nitrogen atom to which they are attached, form a member selected from the group consisting of pyrrolo, pyrrolidino, piperidino, morpholino, thiomorpholino, piperazino, N-(lower alkyl)piperazino, N-hydroxy(lower alkyl)piperazino, N-(lower alkanoyl)piperazino and N-carbo(lower alkoxy)piperazino and the pharmaceutically acceptable acid addition salts of those compounds wherein at least one of $R_1$ and $R_3$ is substituted lower alkyl wherein the substituent is a basic group.

By the terms lower alkyl, lower alkoxy, lower alkanoyloxy and lower alkanoyl are meant those alkyl, alkoxy, alkanoyloxy and alkanoyl groups which contain from 1 to 4 carbon atoms, i.e., those which are conveniently prepared from readily available starting materials.

The compounds of this invention are effective antibacterials both in vitro and in vivo. Additionally, the herein described compounds are effective animal growth promotants, particularly for swine and poultry.

Especially preferred compounds of the present invention include those of the aforesaid formula wherein X is hydrogen, Y is S, SO or $SO_2$, $R_1$ is hydroxy substituted alkyl and $R_2$ and $R_3$ are each hydrogen or lower alkyl. Among these, an especially preferred group includes those wherein $R_2$ is hydrogen and $R_3$ is methyl. An especially preferred group within the latter group includes those wherein Y is $SO_2$ and $R_1$ is hydroxyethyl. Another especially preferred group within said latter group includes those wherein Y is S and $R_1$ is hydroxyethyl.

Another especially preferred group of compounds includes those wherein $R_1$ is alkyl substituted with di(lower alkyl)amino, Y is $SO_2$, X is hydrogen, $R_2$ is hydrogen or lower alkyl and $R_3$ is hydrogen, lower alkyl or substituted lower alkyl wherein the substituent is di(lower alkyl)amino, hydroxy or lower alkoxy. A particularly preferred compound is the compound wherein $R_1$ is 3-piperidinopropyl, Y is $SO_2$, $R_3$ is methyl and each of $R_2$ and X is hydrogen.

The compounds of this invention wherein Y is S may be prepared via either the amide route or via the ester route. The amide route involves (1) bromination (or chlorination) of the corresponding 2-methyl compound to produce the corresponding bromo (or chloro) methyl derivative, (2) conversion of the bromo (or chloro) methyl derivative to the corresponding trimethylammonium methyl compound and (3) replacement of the trimethylammonium group by —$SR_1$. The resulting 3—$CH_2SR_1$ substituted 2-carboxamide-1,4-dioxide compound may then be oxidized to provide the corresponding 3—$CH_2SOR_1$ or 3—$CH_2SO_2R_1$ compounds. In lieu of steps (2) and (3) above, it is also possible to directly replace the bromo (or chloro) group of the bromo (or chloro) methyl substituent with —$SR_1$.

The ester route involves (1) bromination (or chlorination) of an alkyl ester of 3-methyl-2-quinoxaline carboxylic acid 1,4-dioxide, preferably the methyl ester, to produce the corresponding bromo (or chloro) methyl derivative; (2) replacement of the bromo group with —$SR_1$ and (3) amidation of the latter compound to obtain $$-CON\begin{smallmatrix}R_2\\R_3\end{smallmatrix}$$

as the 2-position substituent. If the desired 3-position substituent is —$CH_2SOR_1$ or —$CH_2SO_2R_1$, then the alkyl ester of the 3-$CH_2SR_1$ substituted 2-quinoxaline carboxylic acid 1,4-dioxide is oxidized to obtain the desired 2-position substituent and the resulting sulfoxide or sulfone is amidated to the desired product.

The 3-methyl substituted starting materials for the amide route are well known in the art and can be obtained in accordance with the methods disclosed in U.S. Pat. Nos. 3,557,109 and 3,644,360 and various patents and publications incorporated by reference therein. The 3-methyl substituted starting materials for the ester route are also well known in the art and may be prepared in accordance with the disclosure of U.S. Pat. No. 3,753,987 and various patents and publications incorporated therein by reference.

DETAILED DESCRIPTION OF THE INVENTION

The above-described amide route for preparing the compounds of this invention is schematically depicted hereinafter in Table A and the above-described ester route is schematically depicted in Table B presented hereinafter.

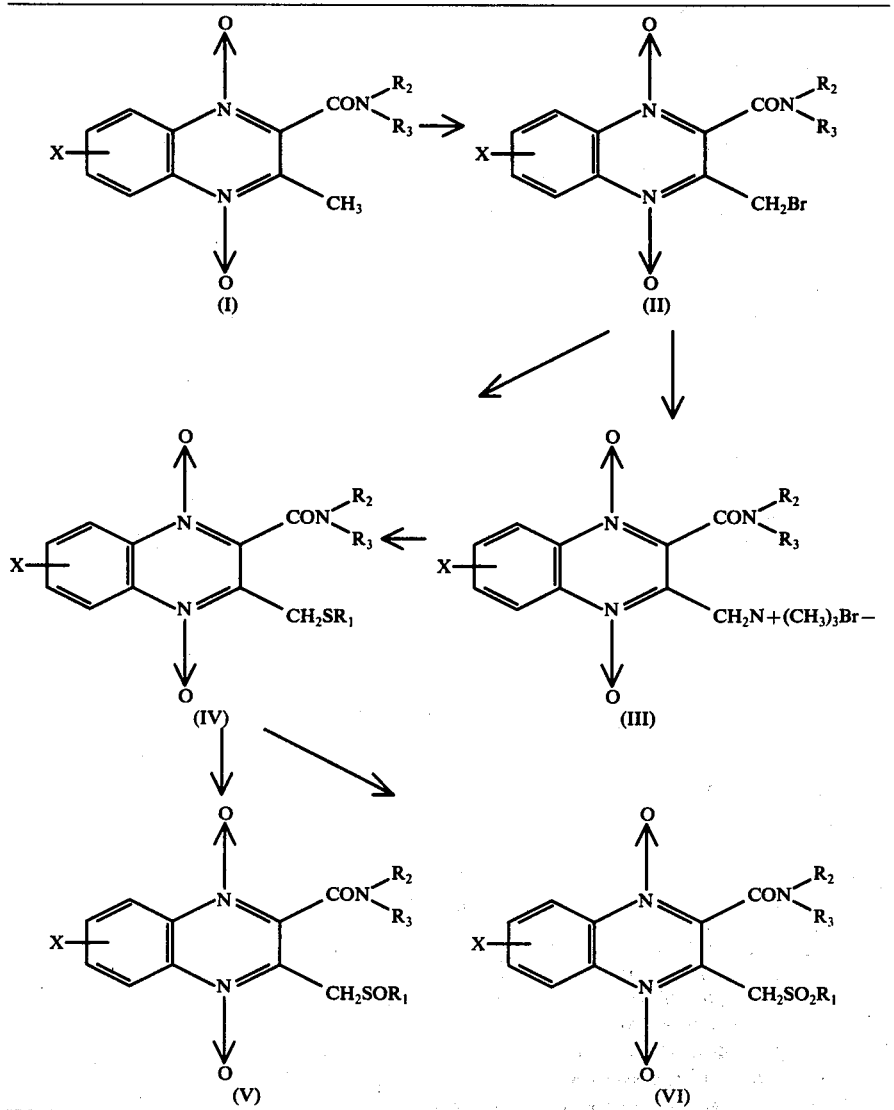

Table A - Amide Route

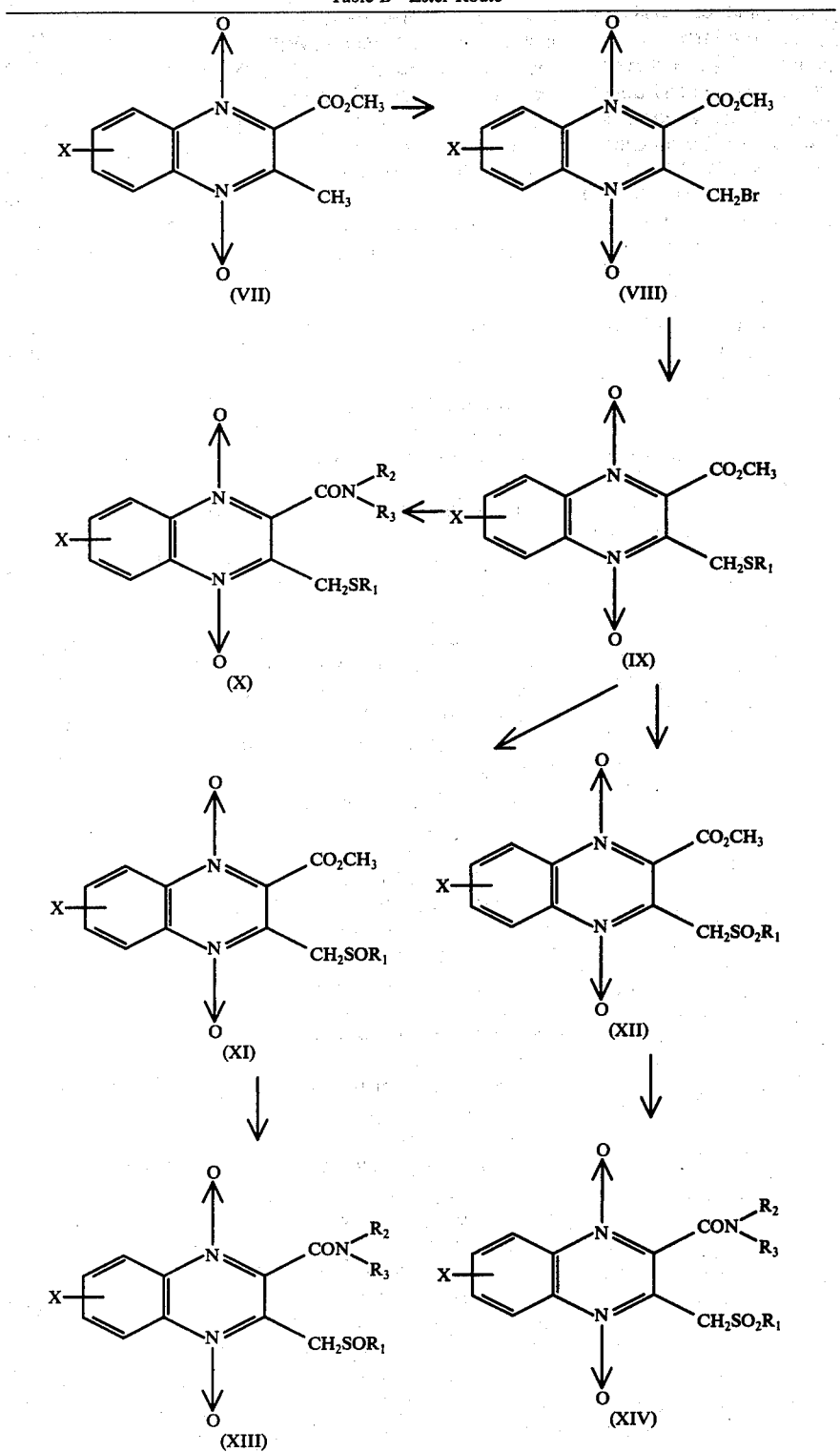

Table B - Ester Route

The starting materials, I, for the amide route are converted to the corresponding 3-bromo (or chloro) methyl substituted compounds, II, by direct halogenation, molecular bromine or chlorine being especially convenient agents to use. One procedure comprises mixing from 1 to 2 molar proportions of I and halogenating agent in chloroform or other chlorinated solvent such as methylene chloride, carbon tetrachloride and chlorobenzene. Additionally, solvents such as formic and acetic acids may also be used. The reaction generally is conducted at a temperature from about 20° to 120° C., preferably about 60° to 100° C., for a period of from about 1 to about 4 hours.

The trimethylammonium derivatives, III, are prepared by treating the appropriate 3-bromo (or chloro) metyl compound, II, with trimethylamine. This reaction is conducted in a suitable diluent or solvent such as N,N-dimethylformamide, ethanol, benzene, xylene, chloroform, dioxane or tetrahydrofuran at temperatures from about 20° to about 100° C., preferably from about 20° to 60° C. Trimethylamine is bubbled into a stirred mixture of the diluent and appropriate reactant II until the mixture is saturated. The exothermic reaction is stirred from about ½ to about 4 hours and the product recovered by filtration or evaporation of the diluent.

Replacement of the trimethylammonium group by —$SR_1$ is accomplished by reacting it with the appropriate mercaptan ($R_1SH$) in the presence of aqueous sodium or potassium hydroxide. The mercaptan is mixed with a two-phase system of aqueous sodium or potassium hydroxide and an organic solvent such as chloroform and then the trimethylammonium substituted compound, III, is added followed by stirring for from 1 to about 4 hours. The organic solvent phase separates and the 3—$CH_2SR_1$ substituted compound, IV, is recovered by removal of the solvent. The latter compound can then be converted to the corresponding 3—$Ch_2SOR_1$ substituted compound, V, or to the 3—$CH_2SO_2R_1$ substituted compound, VI, by oxidation with potassium permanganate, an organic peroxide or an organic peracid such as peracetic, perphthalic, perbenzoic or m-chloroperbenzoic acid. The latter peracid is especially useful since by-product m-chlorobenzoic acid is easily removed. The oxidation is conducted in a solvent such as chloroform or methylene chloride at from about 0° to about 30° C. until one or two equivalents (depending upon whether the sulfinyl or sulfonyl derivative is desired) of the oxidizing agent is consumed. It is advantageous when producing the sulfinyl derivative to use equimolar proportions of reactants in order to avoid or minimize further oxidation. An excess of 5 to 10% of the oxidizing agent is generally used when the sulfonyl derivative is the desired product.

An alternative procedure which may be employed in the amide route involves direct conversion of the 3-bromomethyl reactant, II, to the 3—$CH_2SR_1$ substituted compound, IV. This procedure involves dissolving or slurrying the starting material, II, in an organic solvent such as chloroform, adding at least an equimolar amount of a mercaptan of the formula $R_1SH$ followed by the addition of an acid binding agent such as triethylamine at a rate which suitably controls the exothermic reaction. Following the reaction, the desired product, IV, is recovered.

The starting materials, VII, for the ester route are converted to the corresponding 3-bromo (or chloro) methyl substituted compounds, VIII, by direct halogenation, molecular bromine or chlorine being especially convenient agents to use. One procedure involves introducing bromine (or chlorine) into a slurry of VII in a water-miscible solvent such as dimethylformamide, stirring the reaction mixture until completion and then extracting the product, VIII, with a solvent such as chloroform and recovering the product from the chloroform.

Conversion of intermediate VIII to intermediate IX involves replacement of bromine with $SR_1$ and may be accomplished by several different procedures. One option involves the dropwise addition of triethylamine to an equimolar mixture of VIII and $R_1SH$ in a solvent such as chloroform and recovery of the desired product, IX, from the chloroform layer after washing with water. The second option is similar to the first, but involves the use of an excess of the $R_1SH$ reactant and the substitution of excess diisopropylethylamine for triethylamine. In accordance with this option, dropwise addition is not necessary. Recovery of the desired product is the same as that described in connection with the first option. The third option is the same as the first, except for the use of a reaction medium such as methanol and the substitution of an inorganic base such as sodium or potassium hydroxide for the triethylamine. The required amount of inorganic base is introduced initially.

Conversion of intermediate IX to final product X is via amidation with a reactant of the formula

and is carried out in conventional fashion by introducing the reactants into a suitable solvent such as water, methanol or acetonitrile. An excess of the amine reactant should, of course, be employed and the reaction generally proceeds at a sufficient rate by allowing it to stand at room temperature.

Conversion of intermediate IX to intermediates XI and XII is carried out by the same method described above for converting IV to V or VI in the amide route. Intermediates XI and XII may then be converted, respectively, to final products XIII and XIV by amidation as described immediately above.

Acid addition salts of the compounds of the present invention which contain a basic group are prepared by methods well known to those skilled in the art. A convenient method comprises dissolving the free base in a suitable solvent, e.g., acetone, water, a lower alkanol such as ethanol or isopropanol, containing the desired acid or to which the desired acid is subsequently added. The salts are recovered by filtration, precipitation with a non-solvent, by evaporation of the solvent or, in the case of aqueous solutions, by lyophilization. In this manner, the sulfate, nitrate, phosphate, acetate, propionate, butyrate, citrate, gluconate, benzoate, pamoate, amsonate, tartrate, 3-hydroxy-2-naphthoate, the sulfosalicylate and other salts can be prepared.

The products of this invention are remarkably effective in treating a wide variety of pathogenic microorganisms and are, therefore, useful as industrial antimicrobials, for example, in water treatment, slime-control, paint preservation and wood preservation as well as for topical application purposes as disinfectants.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media, that is, media which have no harmful effect on the active ingredient. For such purposes, it will generally be acceptable to employ concentrations of active ingredients of from about 0.01 percent to about 10 percent by weight based on total composition.

The compounds described herein, in contrast to the usual gram-negative activity of quinoxaline-di-N-oxides, exhibit broad spectrum activity, that is, activity against both gram-negative and gram-positive bacteria, such as *Staphylococcus aureus, Streptomyces pyogenes, Escherichia coli* and *Pasturella multocida*.

When used in vivo for such purposes, these novel compounds can be administered orally or parenterally, e.g., by subcutaneous or intramuscular injection, at a dosage of from about 1 mg./kg. to about 100 mg./kg. of body weight. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide and other nonaqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition. Other methods include mixing with animal feeds, the preparation of feed concentrates and supplements and dilute solutions or suspensions, e.g., a 0.1 percent solution, for drinking purposes.

The addition of a low level of one or more of the herein described 3-substituted quinoxaline-2-carboxamide-1,4-dioxides to the diet of healthy animals, both ruminant and non-ruminant, such that these animals receive the product over an extended period of time, at a level of from about 1 mg./kg. to about 100 mg./kg. of body weight per day, especially over a major portion of their active growth period, results in an acceleration of the rate of growth and improves feed efficiency (the number of pounds of feed required to produce a pound gain in weight). Included in these two classes of animals are poultry (chickens, ducks, turkeys), cattle, sheep, dogs, cats, swine, rats, mice, horses, goats, mules, rabbits, mink, etc. The beneficial effects in growth rate and feed efficiency are over and above what is normally obtained with complete nutritious diets containing all the nutrients, vitamins, minerals, and other factors known to be required for the maximum healthy growth of such animals. The animals thus attain market size sooner and on less feed.

The feed compositions described herein have been found to be particularly valuable and outstanding in the case of swine. In some instances the degree of response may vary with respect to the sex of the animals. The products may, of course, be administered in one component of the feed or they may be blended uniformly throughout a mixed feed; alternatively as noted above, they may be administered in an equivalent amount via the animal's water ration. It should be noted that a variety of feed components may be of use in the nutritionally balanced feeds. Any animal feed composition may be prepared to comprise the usual nutritional balance of energy, proteins, minerals and vitamins together with one or more of the quinoxaline-di-N-oxides described above. Some of the various components are commonly grains such as ground grain and grain by-products; animal protein substances, such as meat and fish by-products; vitaminaceous mixtures, e.g., vitamin A and D mixtures, riboflavin supplements and other vitamin B complexes; and bone meal, limestone and other inorganic compounds to provide minerals.

The relative proportions of the present compounds in feeds and feed concentrates may vary somewhat, depending upon the compound, the feed with which they are employed and the animal consuming the same. These substances are advantageously combined in such relative proportions with edible carriers as to provide pre-mixes or concentrates which may readily be blended with standard nutritionally balanced feeds or which may be used themselves as an adjunct to normal feedings.

In the preparation of concentrates, a wide variety of carriers such as soybean oil meal, corn gluten meal, cotton seed oil meal, sunflower seed meal, linseed oil meal, cornmeal, limestone and corncob meal can be employed to facilitate uniform distribution of the active materials in the finished feed with which the concentrate is blended. The concentrate may be surface coated, if desires, with various proteinaceous materials of edible waxes, such as zein, gelatin, microcrystalline wax and the like to provide a protective film which seals in the active ingredients. The proportions of the drug preparation in such concentrates are capable of wide variation since the amount of active materials in the finished feed may be adjusted by blending the appropriate proportion of concentrate with the feed to obtain the desired degree of supplementation. In the preparation of high potency concentrates, i.e., pre-mixes, suitable for blending by feed manufacturers to produce finished feeds or concentrates of lower potency, the drug content may range from about 0.1 g. to 50 g. per pound of concentrate. The high potency concentrates may be blended by the feed manufacturer with proteinaceous carriers, such as soybean oil meal, to produce concentrated supplements which are suitable for direct feeding to animals. The proportion of the drug in these supplements may vary from about 0.1 to 10 g. per pound of supplement. A particularly useful concentrate is provided by blending 2 g. of drug with 1 pound of limestone-soybean oil meal (1:1). Other dietary supplements, such as vitamins, minerals, etc. may be added to the concentrates in the appropriate circumstances.

The concentrates described may also be added to animal feeds to produce a nutritionally balanced, finished feed containing from about 5 to about 125 g. of the herein described compounds per ton of finished feed. In the case of ruminants, the finished feed should contain protein, fat, fiber, carbohydrate, vitamins and minerals, each in an amount sufficient to meet the nutritional requirements of the animal for which the feed is intended. Most of these substances are present in naturally occurring feed materials, such as alfalfa, hay or meal, cracked corn, whole oats, soybean oil meal, corn silage, ground corn cobs, wheat bran and dried molasses. Bone meal, limestone, iodized salt and trace minerals are frequently added to supply the necessary minerals and urea to provide additional nitrogen.

As is well known to those skilled in the art, the types of diets are extremely variable depending upon the purpose, type of feeding operation, species, etc. Specific diets for various purposes are listed by Morrison in the Appensix of "Feeds and Feeding", the Morrison Publishing Company, Clinton, Iowa, 1959. In the case of non-ruminant animals, such as hogs, a suitable feed may contain from about 50 to 80 percent of grains, 3 to 10 percent animal protein, 5 to 30 percent vegetable protein, 2 to 4 percent of minerals, together with supplementary vitaminaceous sources.

Biological data illustrating the activity of representative compounds and working examples demonstrating the preparation of representative compounds of the present invention appear hereinafter. In this biological data, and in the working examples, standard abbreviations are used for certain radicals. These include: Me for methyl, Et for ethyl, Pr for normal propyl, Bu for normal butyl, $\phi$ for phenyl and Ac for acetyl.

The in vitro antibacterial activity of the quinoxaline-1,4-dioxides of the instant invention is demonstrated by the conventional two-fold serial dilution technique in Brain-Heart Infusion Broth (Difco). The broth is inoculated with bacteria and with the test quinoxaline-1,4-dioxide and then it is incubated overnight under anerobic conditions. On the next day, the test is read visually. The minimum inhibitory concentration (MIC) of test compound is the lowest concentration which prevents turbidity, i.e., which prevents growth of the microorganism.

In determining the in vivo activity of the quinoxaline-1,4-dioxides of this invention, the test compound is administered to mice which have been infected by intraparenteral injection of a lethal inoculum of pathogenic bacteria. The test compound is administered using a multiple dosing regimen and using either the oral (PO) or the subcutaneous (SC) route. The inoculum of bacteria varies from about 1 to about 10 times the amount needed to kill 100% of the mice under the conditions of the test. At the end of the test, the activity of the compound is assessed by counting the number of survivors among the treated animals.

In vitro and in vivo activity of representative compounds of this invention, determined as aforesaid, are reported in the following tabulation for compounds of the formula:

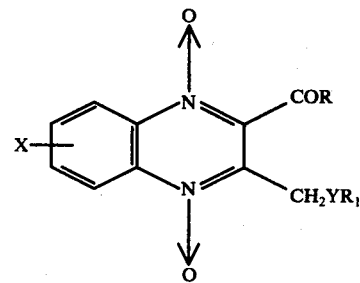

| R | —Y—R$_1$ | X | IN VITRO MIC (mcg./ml.) Strep. pyrogens | E. coli | IN VIVO (a) PO(b) 50 mg./kg. Strep. pyogenes | 25 mg./kg. E. coli |
|---|---|---|---|---|---|---|
| NHMe | —SCH$_2$CH$_2$OH | H | 0.781 | 0.781 | 10/10 (6/10) | 10/10 |
| NHCH$_2$CH$_2$OH | —SCH$_2$CH$_2$OH | H | 12.5 | 50 | 3/10 (5/10) | 0/10 |
| NHPr | —SCH$_2$CH$_2$OH | H | 6.25 | 25 | 5/10 (3/10) | 2/10 |
| NHCH$_2$CH$_2$CH$_2$OH | —SCH$_2$CH$_2$OH | H | 25 | 50 | 1/10 (3/10) | 2/10 |
| NHCH$_2$CH$_3$ | —SCH$_2$CH$_2$OH | H | 3.125 | 6.25 | 2/10 (2/10) | 4/10 |
| NHBu | —SCH$_2$CH$_2$OH | H | 50 | 50 | 2/10 (1/10) | 0/10 |
| NHCH$_3$ | —SO$_2$CH$_2$CH$_2$OH | H | 1.562 | 0.781 | 8/10 (4/10) | 10/10 |
| NH(CH$_2$)$_3$N(Et)$_2$(c) | —SO$_2$CH$_2$CH$_2$OH | H | 200 | >200 | 1/10 | 5/10 |
| NHCH$_2$CH$_2$N(CH$_3$)$_2$ (c) | —SO$_2$CH$_2$CH$_2$OH | H | 100 | 50 | 2/10 | 0/10 |
| NHCH$_2$CH$_2$N(CH$_3$)$_2$(c) | —SO$_2$CH$_2$CH$_2$OH | Cl | 50 | 100 | 2/10 | 2/10 |
| NHEt | —SO$_2$CH$_2$CH$_2$OH | H | 1.562 | 6.25 | 6/10 (8/10) | 9/10 |
| NHCH$_2$CH$_2$OH | —SO$_2$CH$_2$CH$_2$OH | H | 25 | 100 | 3/10 (1/10) | 1/10 |
| NHPr | —SO$_2$CH$_2$CH$_2$OH | H | 3.125 | 3.125 | 4/10 (7/10) | 2/10 |
| NHCH$_2$CH$_2$CH$_2$OH | —SO$_2$CH$_2$CH$_2$OH | H | 12.5 | 100 | 4/10 (5/10) | 0/10 |
| NH$_2$ | —SO$_2$CH$_2$CH$_2$OH | H | 6.25 | 12.5 | 4/10 (8/10) | 0/10 |
| NHCH$_2$CH$_2$OCH$_3$ | —SO$_2$CH$_2$CH$_2$OH | H | 0.781 | 12.5 | 4/10 (0/10) | 0/10 |
| NHCH$_2$CHOHCH$_2$OH | —SO$_2$CH$_2$CH$_2$OH | H | 6.25 | 200 | 4/10 (7/10) | 0/10 |
| NHBu | —SO$_2$CH$_2$CH$_2$OH | H | 1.562 | 25 | 0/10 (4/10) | 4/10 |
| NHCH$_2$CHOHCH$_3$ | —SO$_2$CH$_2$CH$_2$OH | H | 12.5 | 100 | 0/10 (1/10) | 2/10 |
| NHCH$_2$$\phi$ | —SO$_2$CH$_2$CH$_2$OH | H | 0.781 | 200 | 2/10 (2/10) | 2/10 |
| NHCHEtCH$_2$OH | —SO$_2$CH$_2$CH$_2$OH | H | 3.125 | 200 | 0/10 (8/10) | 1/10 |
| NH(CH$_2$)$_4$$\phi$ | —SO$_2$CH$_2$CH$_2$OH | H | 3.125 | >200 | 1/10 (1/10) | 2/10 |
| NHMe | —SCH$_2$CH$_2$CH$_2$OH | H | 1.562 | 12.5 | 0/10 (1/10) | 2/10 |
| NHMe | —SO$_2$CH$_2$CH$_2$CH$_2$OH | H | 3.125 | 12.5 | 9/10 (3/10) | 7/10 |
| NHCH$_3$ | —SCH$_2$CO$_2$Et | H | 12.5 | 12.5 | 0/10 (0/10) | 3/10 |
| NHCH$_3$ | —SO$_2$CH$_2$CH$_2$OAc | H | <0.391 | 3.125 | 9/10 (7/10) | 8/10 |
| NHCH$_2$CH$_2$OH | —S(CH$_2$)$_3$OAc | H | 6.25 | 100 | 1/10 (3/10) | 3/10 |
| NHCH$_3$(c) | —SO$_2$(CH$_2$)$_3$N(CH$_3$)$_2$ | H | 3.125 | 6.25 | 10/10 | 10/10 |
| NHCH$_2$CH$_3$ | —SO$_2$(CH$_2$)$_3$N(CH$_3$)$_2$ | H | 1.562 | 12.5 | 10/10 (10/10) | 10/10 |
| NHCH$_2$CH$_2$SCH$_2$CH$_3$ | —SO$_2$CH$_2$CH$_2$OH | H | 1.562 | 100 | 1/10 (0/10) | 5/10 |
| NHCH$_2$CHCH$_2$OCH$_3$<br>　$\vert$<br>　CH$_3$ | —SO$_2$CH$_2$CH$_2$OH | H | 0.781 | 25 | 8/10 (1/10) | 1/10 |
| NHCH$_2$CH$_3$ | —SO$_2$CH$_2$CH$_2$CH$_2$OH | H | <0.39 | 6.25 | 8/10 (2/10) | 1/10 |
| NHCH$_2$CH$_3$ | —SCH$_2$CH$_2$CH$_2$OAc | H | 3.125 | 25 | 1/10 (2/10) | 0/10 |
| NHCH$_2$CH$_2$CH$_3$ | —SO$_2$CH$_2$CH$_2$CH$_2$OAc | H | 50 | 200 | 3/10 (0/10) | 0/10 |
| NHCH$_2$CH$_2$OCH$_3$ | —SO$_2$CH$_2$CH$_2$CH$_2$OAc | H | 12.5 | 100 | 2/10 (1/10) | 1/10 |
| NHCH$_2$CH$_2$OH | —SO$_2$(CH$_2$)$_3$N(CH$_3$)$_2$ | H | 50 | 50 | 6/10 (0/10) | 0/10 |
| NHCH$_2$CH$_2$OCH$_3$ | —SO$_2$(CH$_2$)$_3$N(CH$_3$)$_2$ | H | 1.562 | 50 | 10/10 (5/10) | 1/10 |
| NH$_2$ | —SO$_2$(CH$_2$)$_3$N(CH$_3$)$_2$ | H | 1.562 | 25 | 10/10 (2/10) | 5/10 |
| N(CH$_3$)$_2$ | —SO$_2$(CH$_2$)$_3$N(CH$_3$)$_2$ | H | 3.125 | 3.125 | 10/10 (6/10) | 10/10 |
| NHCH$_2$CH$_2$CH$_3$ | —SO$_2$(CH$_2$)$_3$N(CH$_3$)$_2$ | H | 25 | 25 | 10/10 (8/10) | 2/10 |
| NH(CH$_2$)$_3$CH$_3$ | —SO$_2$(CH$_2$)$_3$N(CH$_3$)$_2$ | H | 25 | 25 | 10/10 (8/10) | 5/10 |
| N(CH$_3$)$_2$(c) | —SO$_2$(CH$_2$)$_3$N(CH$_2$CH$_3$)$_2$ | H | 6.25 | 25 | 6/10 (1/10) | 0/10 |
| NH$_2$(c) | —SO$_2$(CH$_2$)$_3$N(CH$_2$CH$_3$)$_2$ | H | 3.125 | 6.25 | 9/10 (5/10) | 8/10 |
| NHCH$_3$ | —SO$_2$(CH$_2$)$_3$N(CH$_2$CH$_3$)$_2$ | H | 12.5 | 25 | 8/10 (0/10) | 4/10 |
| NHCH$_3$(c) | —SO$_2$(CH$_2$)$_4$N(CH$_3$)$_2$ | H | 50 | 50 | — | 4/10 |
| NHCH$_2$CH$_3$(c) | —SO$_2$(CH$_2$)$_4$N(CH$_3$)$_2$ | H | 12.5 | 50 | — | 2/10 |

-continued

| R | −Y−R$_1$ | X | IN VITRO MIC (mcg./ml.) Strep. pyrogens | E. coli | IN VIVO (a) PO[b] 50 mg./kg. Strep. pyogenes | 25 mg./kg. E. coli |
|---|---|---|---|---|---|---|
| NHCH$_3$ | −SO$_2$(CH$_2$)$_3$N⟨pyrrolidine⟩ | H | 3.125 | 6.25 | — | 8/10 |
| NH$_2$ | −SO$_2$(CH$_2$)$_3$N⟨pyrrolidine⟩ | H | 6.25 | 12.5 | — | 5/10 |
| N(CH$_3$)$_2$ | −SO$_2$(CH$_2$)$_3$N⟨pyrrolidine⟩ | H | 3.125 | 6.25 | — | 8/10 |
| NHCH$_2$CH$_3$[c] | −SO$_2$(CH$_2$)$_3$N⟨pyrrolidine⟩ | H | 12.5 | 50 | — | 6/10 |
| NHCH$_2$CH$_3$ | −SO$_2$(CH$_2$)$_3$N⟨morpholine⟩ | H | 12.5 | 25 | 10/10 (8/10) | 6/10 |
| NHCH$_3$ | −SO$_2$(CH$_2$)$_3$N⟨morpholine⟩ | H | 25 | 25 | 10/10 (7/10) | 0/10 |
| N(CH$_3$)$_2$ | −SO$_2$(CH$_2$)$_3$N⟨morpholine⟩ | H | 25 | 25 | 0/10 (1/10) | 2/10 |
| NH$_2$ | −SO$_2$(CH$_2$)$_3$N⟨morpholine⟩ | H | 12.5 | 12.5 | 10/10 (6/10) | 2/10 |
| NHCH$_2$CH$_2$N(CH$_3$)$_2$[c] | −SO$_2$(CH$_2$)$_3$N⟨piperidine⟩ | H | 50 | 100 | — | 4/10 |
| NHCH$_2$CH$_2$OH | −SO$_2$(CH$_2$)$_3$N⟨piperidine⟩ | H | 50 | 25 | 10/10 (2/10) | 2/10 |
| NHCH$_3$ | −SO$_2$(CH$_2$)$_3$N⟨piperidine⟩ | H | 6.25 | 6.25 | 10/10 (7/10) | 10/10 |
| NH$_2$ | −SO$_2$(CH$_2$)$_3$N⟨piperidine⟩ | H | 6.25 | 6.25 | 10/10 (4/10) | 10/10 |
| NHCH$_2$CH$_2$OCH$_3$ | −SO$_2$(CH$_2$)$_3$N⟨piperidine⟩ | H | 1.562 | 50 | 10/10 (10/10) | 2/10 |

-continued

| R | —Y—R₁ | X | IN VITRO MIC (mcg./ml.) | | IN VIVO (a) PO[b] | |
|---|---|---|---|---|---|---|
| | | | | | 50 mg./kg. | 25 mg./kg. |
| | | | Strep. pyrogens | E. coli | Strep. pyogenes | E. coli |
| NHCH₂CH₃ | —SO₂(CH₂)₃N◯ | H | 3.125 | 12.5 | 10/10 (9/10) | 6/10 |
| N(CH₃)₂ | —SO₂(CH₂)₃N◯ | H | 3.125 | 3.125 | 10/10 (10/10) | 9/10 |
| | | | | | Salmonella choleraesuis 50 mg./kg. | |
| NHCH₃ | —SO₂(CH₂)₄N◯ | H | 6.25 | 12.5 | 10/10 | (7/10) |
| N(CH₃)₂ | —SO₂(CH₂)₄N◯ | H | 6.25 | 12.5 | 8/10 | (1/10) |
| NH₂ | —SO₂(CH₂)₄N◯ | H | 12.5 | 25 | 9/10 | (0/10) |
| NHCH₂CH₃ | —SO₂(CH₂)₄N◯ | H | 6.25 | 12.5 | 4/10 | (7/10) |

[a]SC = subcutaneous
[b]PO = data in parenthesis is based on oral administration
[c]Tested as hydrochloride salt The following examples illustrate the preparation of representative compounds of the present invention. The Roman numeral designations therein correspond to the counterpart designations in Tables A and B heretofore presented.

EXAMPLE 1

Salt Formation (II⟶III)

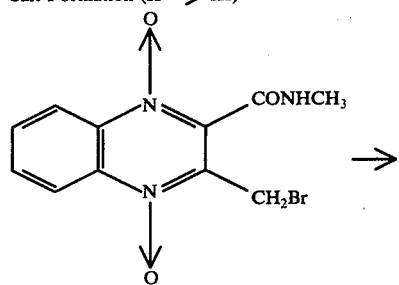
→
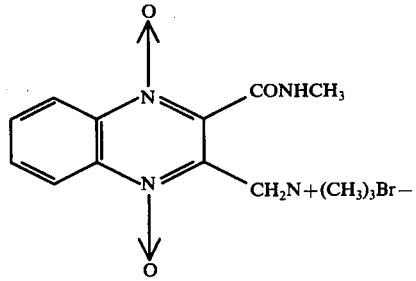

A mixture of 3-bromomethyl-N-methylquinoxaline-2-carboxamide-1,4-dioxide (20.0 g., 0.064 mole) and N,N-dimethylformamide (DMF) (200 ml.) was stirred at room temperature and trimethylamine gas bubbled in for one-half hour. The exothermic reaction was stirred an additional hour and the product recovered by filtration to give 20.4 g. (86% yield); m.p. 195°–196° C.

EXAMPLE 2

Salt Displacement (III⟶IV)

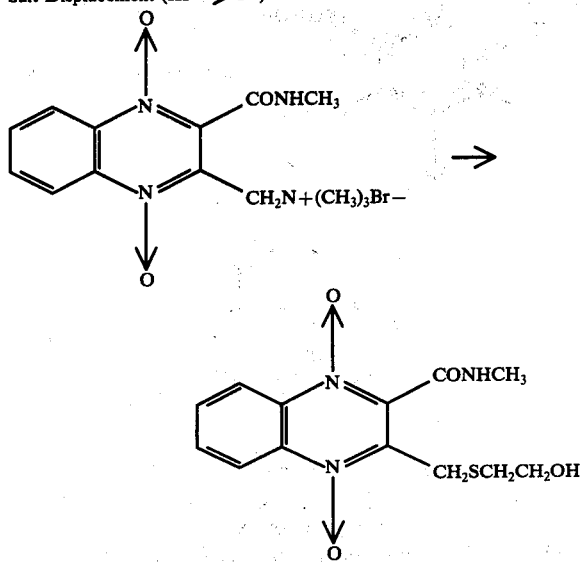

There was added 2-mercaptoethanol (0.84 g., 0.011 mole) to a stirred two-phase system of sodium hydroxide (520 mg., 0.013 mole) in 20 ml. of water and 20 ml. of chloroform. To this mixture was added trimethylammonium salt (2.0 g., 0.005 mole) in small portions. After 20 minutes, the layers were separated and fresh chloroform was added to the aqueous reaction mixture. After 30 minutes the operation was repeated. The chloroform layers were then combined and evaporated to dryness. The resulting solid was triturated with 30 ml. of hexane and the resulting solid was collected to give 0.83 g. (50% yield) of product melting at 160°–164° C. The solid was recrystallized from hot ether-chloroform to give 0.58 g. (35% yield); m.p. 164°–165° C.

EXAMPLE 3

Displacement (II⟶IV)

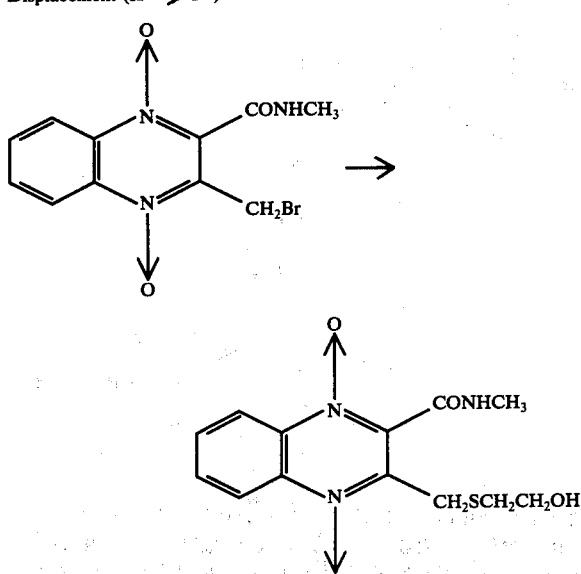

The bromomethyl amide (200 g., 0.64 mole) was added to 2 l. of chloroform in a 5 l. three-necked round-bottomed flask equipped with a mechanical stirrer, addition funnel and thermometer. To the resulting slurry was added 2-mercaptoethanol (54 g., 0.70 mole), followed by the dropwise addition of triethylamine (77.8 g., 0.77 mole) in 100 ml. of chloroform over a 30 minute period. The temperature of the exothermic reaction rose from 24° to 40° C. After stirring the reaction mixture for two hours at ambient temperature, no starting material remained by thin layer chromatography analysis. The mixture was cooled to 15° C. and the solid was collected by suction filtration and washed with two 200 ml. portions of ether. The solid was recrystallized from 1 l. of hot water to yield 119 g. (61%) of yellow needles, m.p. 170°–171° C.

EXAMPLE 4

Oxidation of Sulfide to Sulfoxide (IV⟶V)

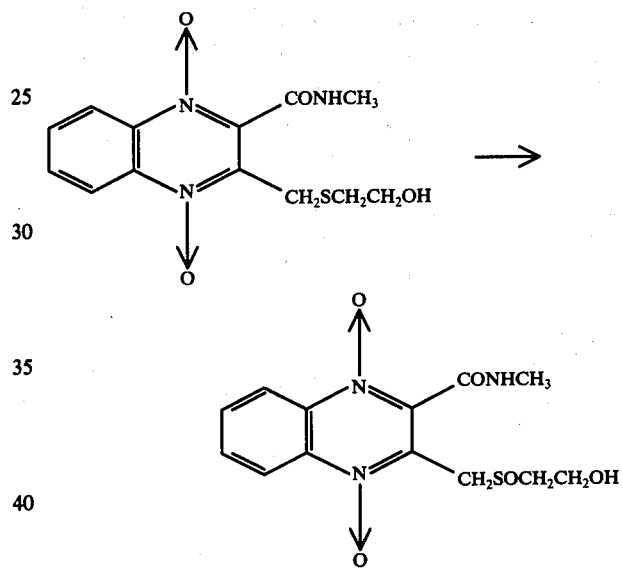

A solution of 9.4 g. (0.0465 mole) of m-chloroperbenzoic acid in 75 ml. of chloroform was added dropwise to a solution of 14.4 g. (0.0465 mole) of the ester sulfide in 100 ml. of chloroform. After 1 hour the reaction mixture was added dropwise to 1.1 l. of diethyl ether and a yellow solid precipitated. The solid was collected by filtration and washed well with 50 ml. of diethyl ether and 100 ml. of hexane and dried.

EXAMPLE 5

Oxidation of Sulfide to Sulfone (IV⟶VI)

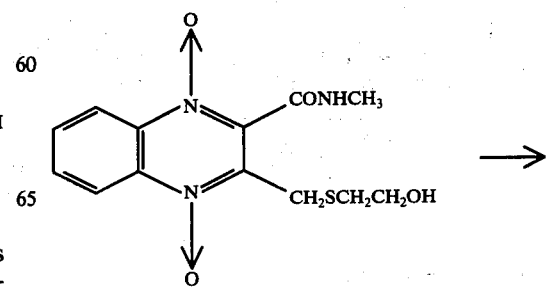

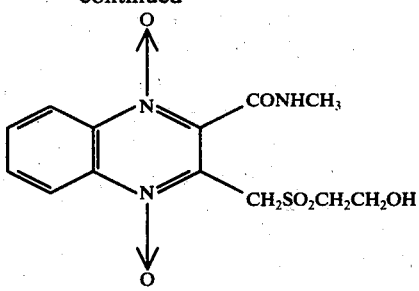

To a slurry of 76 g. (0.245 mole) of the amide sulfide in 900 ml. of chloroform was added in small portions 109 g. (0.539 mole) of 85% m-chloroperbenzoic acid. The temperature of the exothermic reaction rose from 26° to 52° C. and all the solid went into solution. The solution was stirred for 1 hour and then cooled to 18°–20° C. A yellow solid precipitated and it was collected by suction filtration, washed well with 1.5 l. of diethyl ether and dried to yield 75 g. (90% yield); m.p. 188°–190° C.

EXAMPLE 6

Bromination (VII⟶VIII)

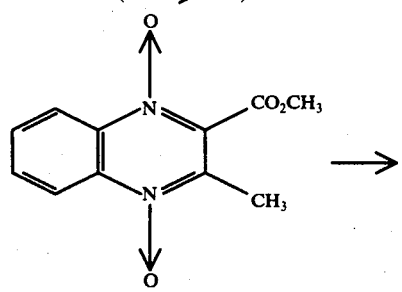

To a thick slurry of 300 g. (1.28 moles) of the ester in 473 ml. of DMF was added with stirring over a period of 2 hours, 64 ml. (1.28 moles) of bromine. The reaction was then stirred for 3 days at room temperature. To the reaction mixture was added 10 l. of ice water and the product was extracted into 1 l. of chloroform. The chloroform layer was dried and concentrated to a thick oil and the oil was poured into 3 l. of diethyl ether. The resulting solid was collected by filtration and dried to give 282 g. (70% yield); m.p. 122°–124° C.

EXAMPLE 7(a)

Displacement (VIII⟶IX) - Option 1

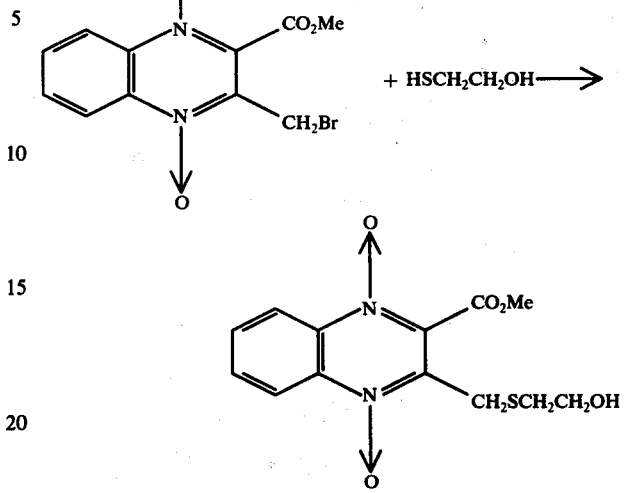

To a solution of bromomethyl ester (100 g., 0.32 mole) and 2-mercaptoethanol (25 g., 0.32 mole) in 1 l. of chloroform was added dropwise a solution of triethylamine (32 g., 0.32 mole) in 300 ml. of chloroform. The reaction temperature rose to 48° C. and at the end of the 1 hour period no starting material remained as shown by thin layer chromatography. The reaction mixture was then washed twice with 300 ml. of water, once with 300 ml. of 5% NaHCO₃ and then twice with 200 ml. of water. The chloroform solution was then dried over sodium sulfate and evaporated to an oil: 90 g. (90% yield). This material was used without further purification in the aminolysis reaction [Examples 10(a) and 10(b)].

EXAMPLE 7(b)

Displacement (VIII⟶IX) - Option 2

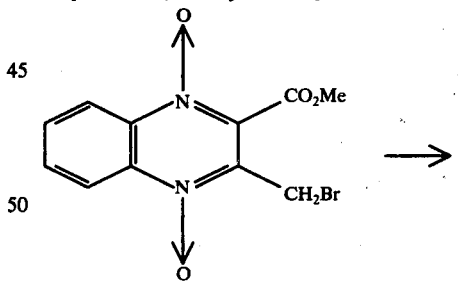

To a solution of 21.7 g. (0.06 mole) of the bromomethyl ester in 250 ml. of chloroform was first added 6.7 ml. (0.09 mole) of 2-mercaptoethanol and secondly 11.6 g. (0.09 mole) of diisopropylethylamine. After 1.5 hours the reaction mixture was washed three times with 200 ml. of 5% sodium bicarbonate solution and twice with 200 ml. of water. The chloroform layer was then dried over anhydrous sodium sulfate and evaporated to give a solid. Trituration with 300 ml. of hexane gave 20 g. (97% yield) of a solid melting at 122°-124° C.

EXAMPLE 8(a)

Oxidation of Sulfide to Sulfone (IX⟶XII) - Option 1

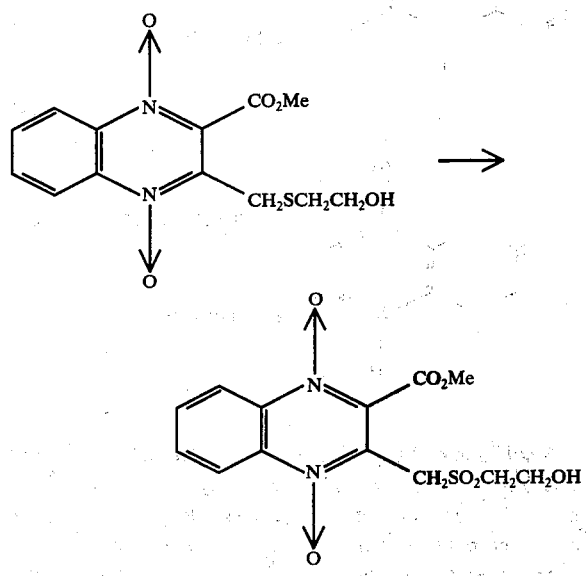

To a solution of 50 g. (0.16 mole) of the ester sulfide in 1 l. of chloroform was added in small portions 50 g. (0.29 mole) of 85% m-chloroperbenzoic acid. When the addition was complete and the chloroform solution had cooled to room temperature, the reaction mixture was diluted to 1 l. with diethyl ether causing a yellow oil to separate. The solvent was decanted and the oil was crystallized from 250 ml. of hot methanol giving 25.5 g. (47% yield); m.p. 129°-131° C.

EXAMPLE 8(b)

Oxidation of Sulfide to Sulfone (IX ⟶XII) - Option 2

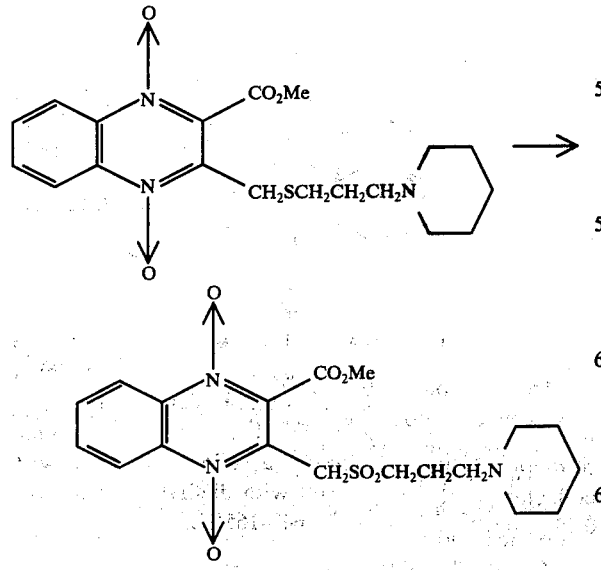

A solution of ester sulfide (26 g., 0.067 mole) in 2N sulfuric acid (170 ml.) and acetone (150 ml.) was cooled to 0° C. with an ice-bath. An aqueous solution of potassium permanganate (22 g. in 500 ml. of water) was added to the reaction mixture over a 45 minute period while the temperature was maintained at 5° C. Five minutes after the addition was complete, the mixture was decolorized with 30% hydrogen peroxide; the pH was kept below 4 with the addition of more 2N sulfuric acid. The reaction mixture was extracted with chloroform (2 × 200 ml.) and the chloroform extract was discarded. The reaction mixture, to which 600 ml. of chloroform had been added, was carefully made slightly basic with solid sodium bicarbonate. The chloroform layer was separated, and the aqueous phase was extracted with more chloroform (2 × 150 ml.). The combined chloroform extracts were dried over anhydrous magnesium sulfate and evaporated in vacuo, leaving a yellow oil (16.0 g., 56% yeild). This material was used without further purification.

EXAMPLE 9

Oxidation of Sulfide to Sulfoxide (IX⟶XI)

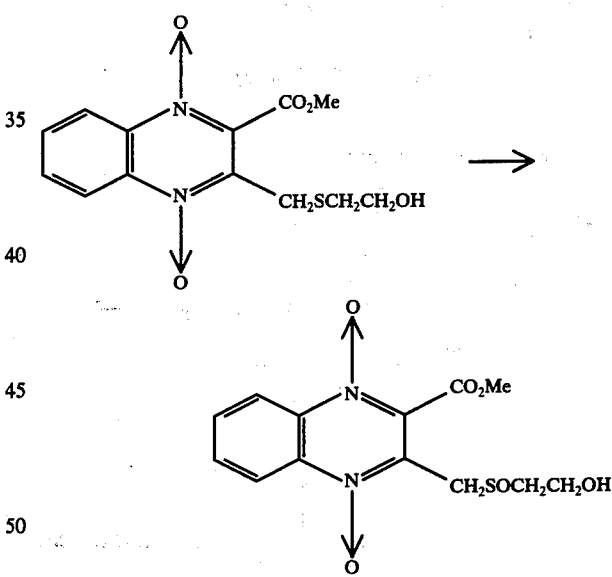

A solution of 9.4 g. (0.0465 mole) of m-chloroperbenzoic acid in 75 ml. of chloroform was added dropwise to a solution of 13.8 g. (0.0465 mole) of the ester sulfide in 100 ml. of chloroform. After 1 hour the reaction mixture was added dropwise to 1.1 liters of diethyl ether and a yellow solid precipitated. The solid was collected by filtration and washed well with 50 ml. of diethyl ether and 100 ml. of hexane and dried.

EXAMPLE 10(a)

Amidation of Sulfide (IX⟶X)

-continued

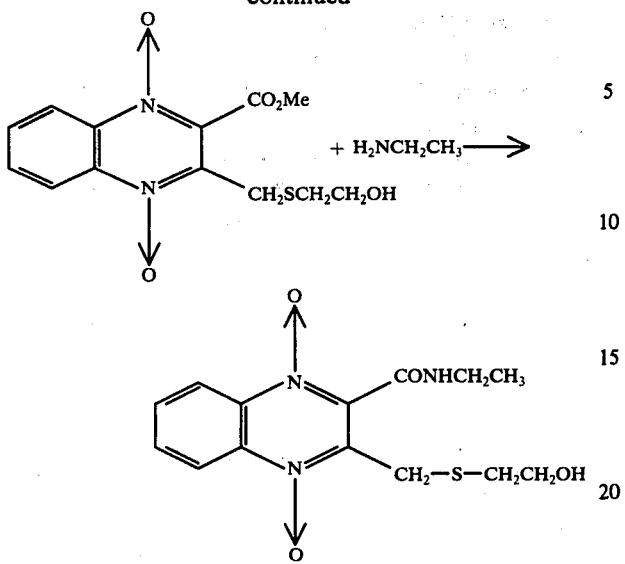

There are dissolved 1.0 g. (0.003 mole) of the ester sulfide in 20 ml. of a 4.1 molar solution of ethylamine in methanol. The solution was gently warmed on a steam bath for 10 minutes and then allowed to sit at room temperature for 3 hours. The flocculent yellow solid which precipitated from the reaction mixture was collected by filtration to give 0.64 g. (60% yeild) which melted at 184°–186° C.

EXAMPLE 10(b)

Amidation of Sulfide (IX⟶X)

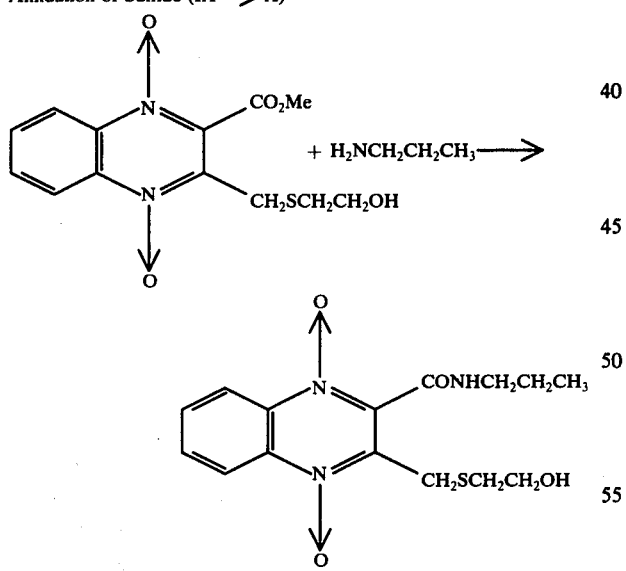

To a solution of 1.0 g. (0.003 mole) of the ester sulfide in 20 ml. of acetonitrile was added 3.0 g. (0.051 mole) of propylamine and the resulting solution was stirred at room temperature for 20 hours. The reaction mixture was then poured into 300 ml. of diethyl ether. A yellow solid was isolated by decanting the ether and triturating with an acetone-ether mixture (4:1). The resulting slurry was filtered to yield 0.35 g. (30% yield); m.p. 180°–181° C.

EXAMPLE 11

Amidation of Sulfoxide (XI⟶XIII)

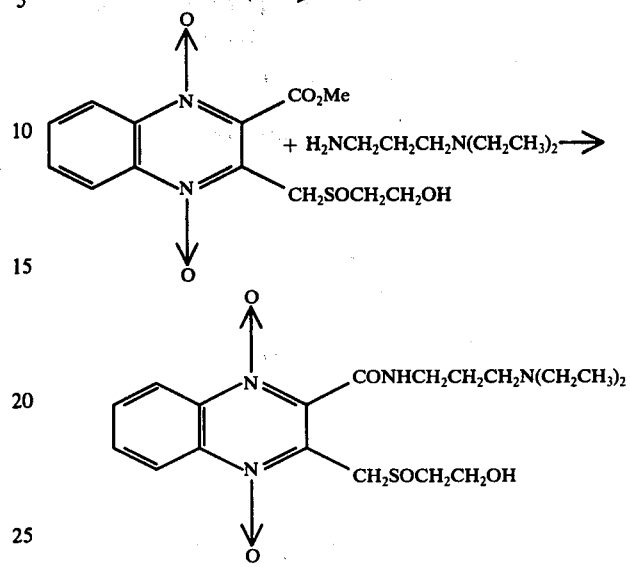

A solution of 1.0 g. (3.2 mmoles) of the ester sulfoxide and 3.0 g. (large excess) of 3-diethylamino-n-propylamine in 20 ml. of acetonitrile was allowed to stand at room temperature for 24 hours. The solution was then evaporated to dryness and the resulting solid was recrystallized from acetone to yield the desired product.

EXAMPLE 12

Amidation of Sulfone (XII⟶XIV)

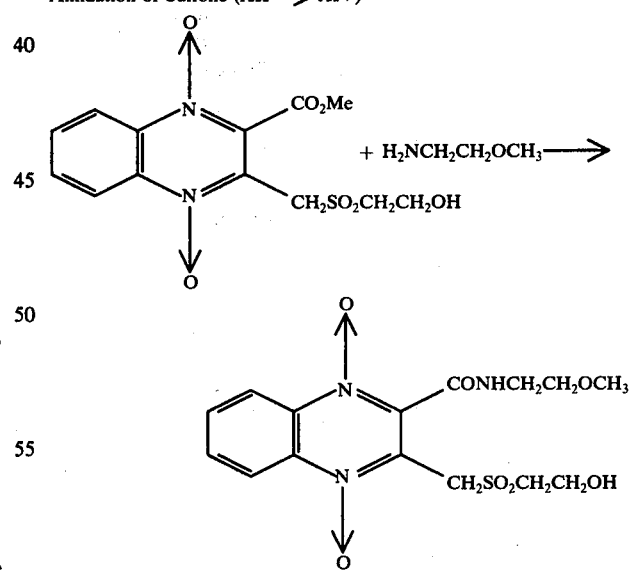

To a solution of 1.0 g. (0.003 mole) of the ester sulfone in 20 ml. of acetonitrile was added 3.0 g. (0.040 mole) of 2-methoxyethylamine. The solution was stirred at room temperature for 20 hours and then poured into 200 ml. of diethyl ether. The resulting yellow precipitate was collected and washed well with diethyl ether to give 0.95 g. (86% yield); m.p. 164°–165° C.

EXAMPLE 13

Compounds of the following formula were prepared by the indicated methods:

[Structure: quinoxaline 1,4-dioxide with 2-COR and 3-CH₂SCH₂CH₂OH substituents]

| R | Method (Table A or B) | Melting Point °C. |
|---|---|---|
| NHMe | II → IV | 173–175 |
| NHCH₂CH₂OH | IX → X | 186–187 |
| NHPr | IX → X | 180–181 |
| NHCH₂CH₂CH₂OH | IX → X | 169–171 |
| NHEt | IX → X | 184–186 |
| NHBu | IX → X | 155–157 |

EXAMPLE 14

Compounds of the following formula were prepared by the indicated methods:

[Structure: X-substituted quinoxaline 1,4-dioxide with 2-COR and 3-CH₂SO₂CH₂CH₂OH substituents]

| R | X | (Table A or B) | Melting Point °C. |
|---|---|---|---|
| NHMe | H | IV → VI | 188–190 |
| NH(CH₂)₃N(Et)₂ | H | XII → XIV | 182–185 |
| NHCH₂CH₂N(Me)₂ | H | XII → XIV | 188–190 |
| NHCH₂CH₂N(Me)₂ | Cl | XII → XIV | 185 |
| NHEt | H | XII → XIV | 174–176 |
| NHCH₂CH₂OH | H | XII → XIV | 198–199 |
| NHPr | H | XII → XIV | 207–208 |
| NHCH₂CH₂CH₂OH | H | XII → XIV | 192–193 |
| NH₂ | H | XII → XIV | 223–225 |
| NHCH₂CH₂OMe | H | XII → XIV | 164–165 |
| NHCH₂CHOHCH₂OH | H | XII → XIV | 179–181 |
| NHBu | H | XII → XIV | 156–157 |
| NHCH₂CH(OH)CH₃ | H | XII → XIV | 197–199 |
| NHCH₂φ | H | XII → XIV | 187–189 |
| NH—CH(Et)CH₂OH | H | XII → XIV | 159–161 |
| NH(CH₂)₄φ | H | XII → XIV | 150–152 |
| NHCH₂CH₂SEt | H | XII → XIV | 115–117 |
| NHCH₂CH(CH₂OMe)CH₃ | H | XII → XIV | 149–150 |

EXAMPLE 15

The following compound was produced by the indicated method:

[Structure: quinoxaline 1,4-dioxide with 2-COR and 3-CH₂SCH₂CH₂CH₂OH substituents]

| R | Method (Table B) | Melting Point °C. |
|---|---|---|
| NHMe | IX → X | 191 |

EXAMPLE 16

Compounds of the following formula were prepared by the indicated method:

[Structure: quinoxaline 1,4-dioxide with 2-COR and 3-CH₂SO₂CH₂CH₂CH₂OH substituents]

| R | Method (Table B) | Melting Point °C. |
|---|---|---|
| NHMe | XII → XIV | 196–197 |
| NHEt | XII → XIV | 166–168 |
| NHCH₂CH₂OH | XII → XIV | 178–180 |

EXAMPLE 17

Compounds of the following formula were prepared by the indicated methods:

[Structure: quinoxaline 1,4-dioxide with 2-COR and 3-CH₂SCH₂CHOHCH₂OH substituents]

| R | Method (Table A or B) | Melting Point °C. |
|---|---|---|
| NHMe | II → IV | 176–177 |
| NHPr | IX → X | 189–190 |
| NHBu | IX → X | 188–190 |

EXAMPLE 18

The following compound was produced by the indicated method:

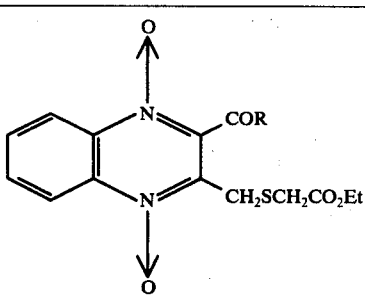

| R | Method (Table A) | Melting Point ° C. |
|---|---|---|
| NHMe | III → IV | 147-148 |

EXAMPLE 19

The following compound was produced by the indicated method:

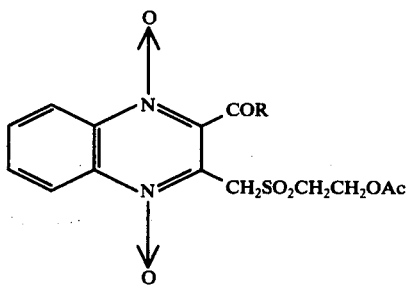

| R | Method (Table B) | Melting Point ° C. |
|---|---|---|
| NHMe | IV → VI | 178-179 |

EXAMPLE 20

Compounds of the following formula were produced by the indicated method:

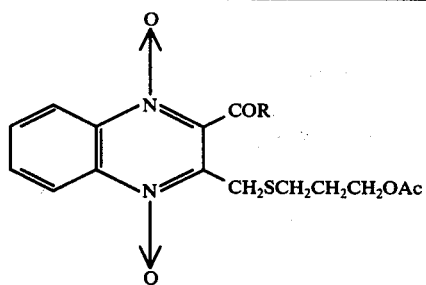

| R | Method (Table B) | Melting Point ° C. |
|---|---|---|
| NHCH$_2$CH$_2$OH | IX → X | 153-155 |
| NHEt | IX → X | 190-192 |

EXAMPLE 21

Compounds of the following formula were prepared by the indicated method:

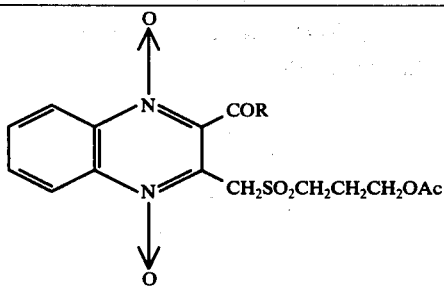

| R | Method (Table B) | Melting Point ° C. |
|---|---|---|
| NHPr | XII → XIV | 159-161 |
| NHBu | XII → XIV | 146-148 |
| NHCH$_2$CH$_2$OMe | XII → XIV | 117-119 |

EXAMPLE 22

The following compounds were prepared by the indicated methods:

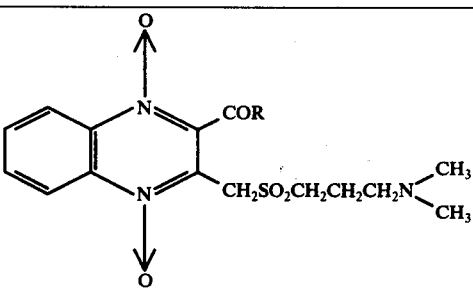

| R | Method (Table A or B) | Melting Point ° C. |
|---|---|---|
| NHMe . HCl | IV → VI | 218-220 |
| NHCH$_2$CH$_3$ | XII → XIV | 145-147 |
| NHCH$_2$CH$_2$OH | XII → XIV | 169-171 |
| NHCH$_2$CH$_2$OCH$_3$ | XII → XIV | 122-124 |
| NH$_2$ | XII → XIV | 178-182 |
| N(CH$_3$)$_2$ | XII → XIV | 170-173 |
| NHCH$_2$CH$_2$CH$_3$ | XII → XIV | 130-133 |
| NH(CH$_2$)$_3$CH$_3$ | XII → XIV | 129-131 |

EXAMPLE 23

The following compounds were prepared by the indicated method:

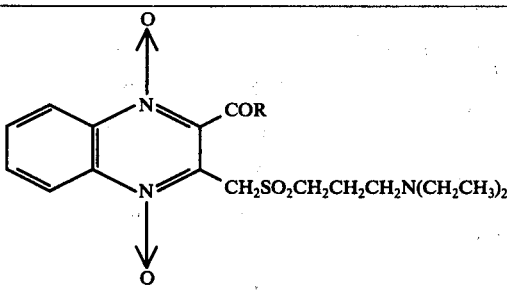

| R | Method (Table B) | Melting Point ° C. |
|---|---|---|
| N(CH$_3$)$_2$ . HCl | XII → XIV | 90-97 |
| NH$_2$ . HCl | XII → XIV | 90-120 |
| NHCH$_3$ | XII → XIV | 158-163 |

EXAMPLE 24

The following compounds were prepared by the indicated method:

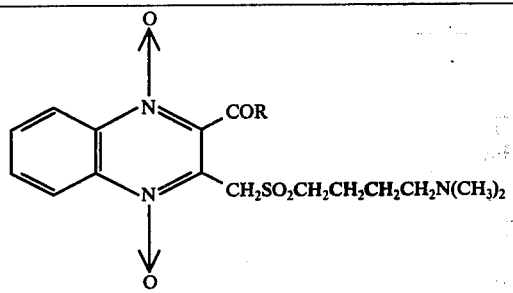

| R | Method (Table B) | Melting Point ° C. |
|---|---|---|
| NHCH$_3$ . HCl | XII → XIV | 158–161 |
| NHCH$_2$CH$_3$ . HCl | XII → XIV | 110–112 |

EXAMPLE 25

The following compounds were prepared by the indicated method:

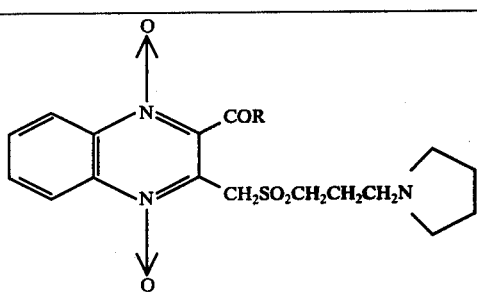

| R | Method (Table B) | Melting Point ° C. |
|---|---|---|
| NHCH$_3$ | XII → XIV | 173–175 |
| NH$_2$ | XII → XIV | 179–180 |
| N(CH$_3$)$_2$ | XII → XIV | 163–167 |
| NHCH$_2$CH$_3$ . HCl | XII  XIV | 70–110 |

EXAMPLE 26

The following compounds were prepared by the indicated method:

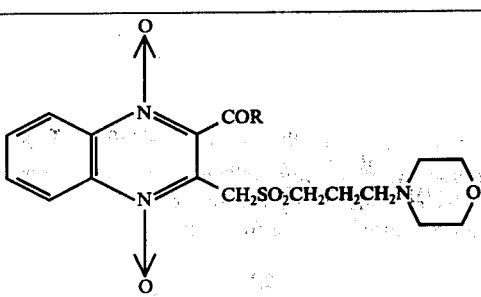

| R | Method (Table B) | Melting Point ° C. |
|---|---|---|
| NHCH$_2$CH$_3$ | XII → XIV | 178–181 |
| NHCH$_3$ | XII → XIV | 144–146 |
| N(CH$_3$)$_2$ | XII → XIV | 140–143 |
| NH$_2$ | XII → XIV | 178–181 |

EXAMPLE 27

The following compounds were prepared by the indicated method:

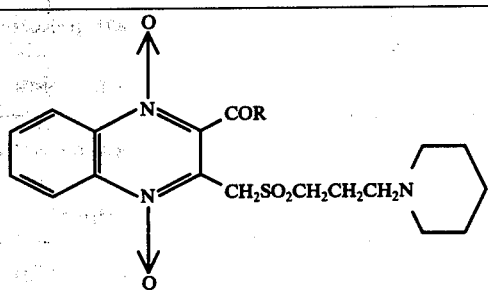

| R | Method (Table B) | Melting Point ° C. |
|---|---|---|
| NHCH$_2$CH$_2$OH | XII→XIV | 140–142 |
| NHCH$_3$ | XII→XIV | 162–165 |
| NH$_2$ | XII→XIV | 174–176 |
| NHCH$_2$CH$_2$OCH$_3$ | XII→XIV | 128–130 |
| NHCH$_2$CH$_3$ | XII→XIV | 139–142 |
| N(CH$_3$)$_2$ | XII→XIV | 169–171 |
| NHCH$_2$CH$_2$N(CH$_3$)$_2$ . HCl | XII→XIV | 100–110 |

EXAMPLE 28

The following compounds were prepared by the indicated method:

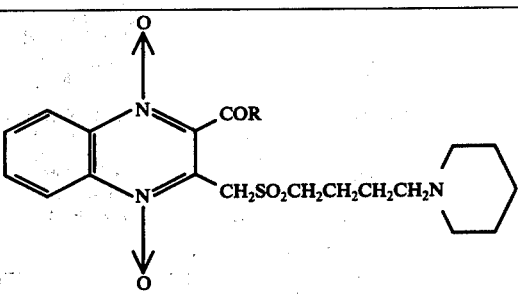

| R | Method (Table B) | Melting Point ° C. |
|---|---|---|
| NHCH$_3$ | XII→XIV | 135–138 |
| N(CH$_3$)$_2$ | XII→XIV | 137–139 |
| NH$_2$ | XII→XIV | 172–176 |
| NHCH$_2$CH$_3$ | XII→XIV | 145–149 |

EXAMPLE 29

The compounds indicated below are prepared by the appropriate previously-described and illustrated methods of Examples 7(b) and 10(a):

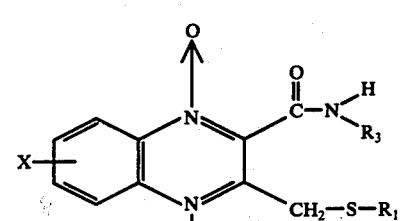

| X | R$_1$ | R$_3$ |
|---|---|---|
| 7-OCH$_3$ | CH$_2$CONH$_2$ | (CH$_2$)$_2$NH$_2$ |

-continued

| X | R₁ | R₃ |
|---|---|---|
| 7-CF₃ | (CH₂)₂CONH(CH₃) | (CH₂)₂NH(CH₃) |
| 6-CH₃ | CH₂CON(CH₃)₂ | (CH₂)₂N(C₂H₅)₂ |
| 7-SCH₃ | (CH₂)₂Cl | |
| 7-SOCH₃ | (CH₂)₂F | (CH₂)₃—NCH₂CH₂CH₂CH₂ |
| | | (CH₂)₂—NCH₂CH₂CH₂CH₂CH₂ |
| 7-SO₂CH₃ | (CH₂)₂SH | |
| | | (CH₂)₂—NCH₂CH₂OCH₂CH₂ |
| H | (CH₂)₂SO₃H | |
| | | (CH₂)₃—NCH₂CH₂N(CH₃)CH₂CH₂ |
| H | (CH₂)₂SCH₃ | |
| | | (CH₂)₂—NCH₂CH₂N(CH₂OH)CH₂CH₂ |
| H | (CH₂)₂SOCH₃ | |
| | | (CH₂)₂—NCH₂CH₂N(COC₄H₉)CH₂CH₂ |
| H | (CH₂)₂SO₂C₄H₉ | |
| | | (CH₂)₂—NCH₂CH₂N(COOC₂H₅)CH₂CH₂ |
| 7-Cl | | |
| | (CH₂)₂—NCH₂CH₂CH₂CH₂ | (CH₂)₃—NCH=CHCH=CH |
| 7-Br | | |
| | (CH₂)₂—NCH₂CH₂OCH₂CH₂ | (CH₂)₄—NCH₂CH₂NHCH₂CH₂ |
| 7-OC₄H₉ | | |
| | (CH₂)₃—NCH₂CH₂CH₂CH₂ | (CH₂)₂—NCH₂CH₂CH₂CH₂CH₂ |
| 6-CH₃ | | CH₂CH(CH₃)CH₂OH |
| | (CH₂)₂—NCH₂CH₂SCH₂CH₂ | |
| H | (CH₂)₂OH | (CH₂)₂SC₂H₅ |
| H | (CH₂)₂OC₂H₅ | CH₂CON(C₂H₅)₂ |
| 7-Cl | (CH₂)₂NH₂ | (CH₂)₂OCCH₃<br>‖<br>O |
| H | (CH₂)₂OH | (CH₂)₂(NH)CC₂H₅<br>‖<br>O |
| H | CH₂COOCH₃ | CH₂CH₂OH |
| 7-Cl | (CH₂)₂COOC₂H₅ | (CH₂)₂N(CH₃)₂ |
| 6-CH₃ | | CH₂COOH |
| | (CH₂)₂—NCH₂CH₂OCH₂CH₂ | |

Oxidation of the above compounds according to the procedures of Examples 4 and 5 affords compounds of the formulae:

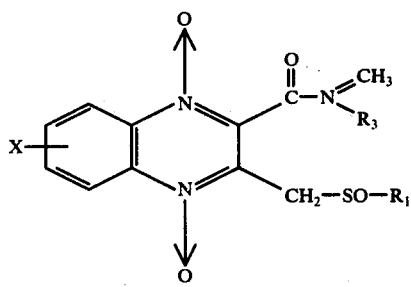

and

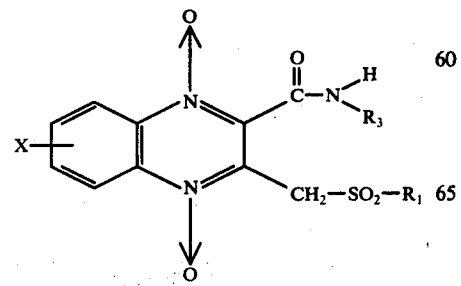

Of course, when R₁ contains an oxidizable group, e.g., SH or SCH₃, said group is also oxidized.

The compounds of the formula

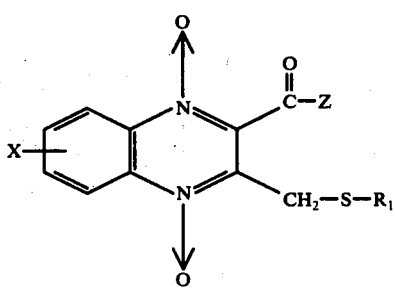

are produced from appropriate reactants by the procedures of Examples 7(a) and 10(a):

| X | R₁ | Z |
|---|---|---|
| H | (CH₂)₂OH | —NCH=CHCH=CH |
| 6-Cl | (CH₂)₂SO₃H | —NCH₂CH₂CH₂CH₂ |
| 7-Br | (CH₂)₂Cl | —NCH₂CH₂CH₂CH₂CH₂ |
| H | (CH₂)₂SCH₃ | —NCH₂CH₂OCH₂CH₂ |
| 6-CF₃ | (CH₂)₂OH | —NCH₂CH₂SCH₂CH₂ |
| 7-SO₂CH₃ | CH₂CONH₂ | —NCH₂CH₂NHCH₂CH₂ |
| H | (CH₂)₃CON(CH₃)₂ | —NCH₂CH₂N(CH₂)CH₂CH₂ |
| H | (CH₂)₃OH | —NCH₂CH₂N(CH₂OH)CH₂CH₂ |
| H | (CH₂)₂OC₂H₅ | —NCH₂CH₂N(COCH₃)CH₂CH₂ |
| 7-F | (CH₂)₂Ot-C₄H₉ | —NCH₂CH₂N(COOC₂H₅)CH₂CH₂ |

The sulfoxide and sulfone analogs of the preceding compounds are prepared in accordance with the previously described methods.

EXAMPLE 30

The acid addition salts of the compounds of the present invention which contain a basic group are prepared by dissolving the appropriate 3-substituted quinoxaline-2-carboxamide-1,4-dioxide (0.01 mol) in ethanol and then adding a stoichiometric amount of the selected acid. The resulting solution is stirred at room temperature for 30 minutes and the acid salt may be recovered by evaporation of the solvent or by precipitation with a nonsolvent, e.g., ether. In this way, the acid addition salts of sulfuric, nitric, phosphoric, acetic, propionic, butyric, citric, gluconic, benzoic, pamoic, amsonic, tartaric, 3-hydroxy-2-naphthoic and sulfosalicylic acid are prepared.

What is claimed is:

1. A compound selected from the group consisting of

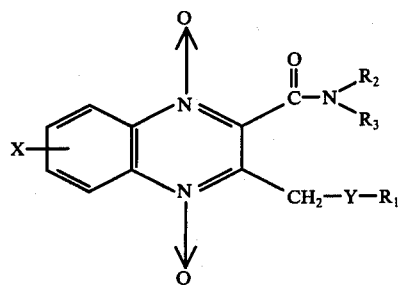

wherein X is a 6- or 7-position substituent selected from the group consisting of hydrogen, halogen, lower alkoxy, trifluoromethyl, methyl, lower alkyl sulfide, lower alkyl sulfoxide and lower alkyl sulfone; Y is S, SO or SO₂; R₁ is selected from the group consisting of carbamyl(lower alkyl), carbo(lower alkoxy)lower alkyl and mono-substituted alkyl having from 2 to 4 carbon atoms in the alkyl group wherein the substituent is selected from the group consisting of hydroxy, lower alkoxy, amino, mono(lower alkyl)amino, di(lower alkyl)amino, mono(lower alkyl)carbamyl, di(lower alkyl)carbamyl, halogen, mercapto, sulfo, lower alkyl sulfide, lower alkyl sulfoxide, lower alkyl sulfone, acetoxy, pyrrolidino, piperidino, morpholino, thiomorpholino, piperazino, N-(lower alkyl)piperazino, N-hydroxy(lower alkyl)piperazino, N-(lower alkanoyl)piperazino and N-carbo(lower alkoxy)piperazino; R₂, when taken separately, is hydrogen or lower alkyl; R₃, when taken separately, is hydrogen, lower alkyl or mono-substituted lower alkyl wherein the substituent is phenyl, amino, mono(lower alkyl)amino, di(lower alkyl)amino, pyrrolidino, piperidino, morpholino, N-(lower alkyl)piperazino, N-hydroxy(lower alkyl)piperazino, N-(lower alkanoyl)piperazino, N-carbo(lower alkoxy)piperazino, pyrrolo, piperazino, imidazolidino, hydroxy, lower alkoxy, thio(lower alkyl), carboxy, carbo(lower alkoxy), carbamyl, mono(lower alkyl)carbamyl, di(lower alkyl)carbamyl, lower alkanoyloxy or lower alkanoylamino and R₂ and R₃, when taken together with the nitrogen atom to which they are attached, form a member selected from the group consisting of pyrrolo, pyrrolidino, piperidino, morpholino, thiomorpholino, piperazino, N-(lower alkyl)piperazino, N-hydroxy(lower alkyl)piperazino, N-(lower alkanoyl)piperazino and N-carbo(lower alkoxy)- piperazino and the pharmaceutically acceptable acid addition salts of those compounds wherein at least one of $R_1$ and $R_3$ is substituted lower alkyl wherein the substituent is a basic group.

2. A compound of claim 1 wherein X is hydrogen, Y is S, SO or $SO_2$, $R_1$ is lower alkyl, mono-substituted with hydroxy, and $R_2$ and $R_3$ are each hydrogen or lower alkyl.

3. The compound of claim 2 wherein $R_2$ is hydrogen and $R_3$ is methyl.

4. The compound of claim 3 wherein Y is $SO_2$ and $R_1$ is hydroxyethyl.

5. The compound of claim 3 wherein Y is S and $R_1$ is hydroxyethyl.

6. The compound of claim 1 wherein X is hydrogen, Y is S, SO or $SO_2$, $R_1$ is lower alkyl mono-substituted with di(lower alkyl)amino, $R_2$ is hydrogen or lower alkyl and $R_3$ is hydrogen, lower alkyl or lower alkyl substituted with di(lower alkyl)amino, hydroxy or lower alkoxy.

7. The compound of claim 6 wherein Y is $SO_2$, $R_1$ is 3-dimethylaminopropyl, $R_2$ is hydrogen and $R_3$ is methyl.

8. The compound of claim 6 wherein Y is $SO_2$, $R_1$ is 3-dimethylaminopropyl, $R_2$ is hydrogen and $R_3$ is ethyl.

9. The compound of claim 1 wherein Y is $SO_2$, $R_1$ is 3-pyrrolidinopropyl, $R_2$ is hydrogen, and $R_3$ is methyl and X is hydrogen.

10. The compound of claim 1 wherein Y is $SO_2$, $R_1$ is 3-piperidinopropyl, $R_2$ is hydrogen, $R_3$ is methyl and X is hydrogen.

* * * * *